(12) United States Patent
Nangi et al.

(10) Patent No.: US 12,221,440 B2
(45) Date of Patent: Feb. 11, 2025

(54) PROCESS FOR THE PREPARATION OF TRAMETINIB ACETIC ACID SOLVATE

(71) Applicant: Aurobindo Pharma Ltd., Hyderabad (IN)

(72) Inventors: Gangadhara Bhima Shankar Nangi, Hyderabad (IN); Ramadas Chavakula, Hyderabad (IN); Venkata Rama Krishna Murthy Moturu, Hyderabad (IN); Jyothi Sudharshan Chakradhar Saladi, Hyderabad (IN); Sandeep Kumar Vadla, Hyderabad (IN); Sadashiv Jagtap, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 808 days.

(21) Appl. No.: 17/427,633

(22) PCT Filed: Feb. 6, 2020

(86) PCT No.: PCT/IB2020/050942
§ 371 (c)(1),
(2) Date: Jul. 31, 2021

(87) PCT Pub. No.: WO2020/061654
PCT Pub. Date: Aug. 13, 2020

(65) Prior Publication Data
US 2022/0098192 A1    Mar. 31, 2022

(30) Foreign Application Priority Data
Feb. 6, 2019  (IN) .............................. 201941004635

(51) Int. Cl.
*C07D 471/04* (2006.01)
*A61K 31/519* (2006.01)

(52) U.S. Cl.
CPC ........ *C07D 471/04* (2013.01); *C07B 2200/13* (2013.01)

(58) Field of Classification Search
CPC ........................... C07D 471/04; A61K 31/519
USPC ........................................ 544/279; 514/264.1
See application file for complete search history.

(56) References Cited

U.S. PATENT DOCUMENTS 7,378,423 B2 *  5/2008  Kawasaki ............. C07C 275/50
                                                              544/279
9,181,243 B2 * 11/2015  Hu ....................... C07D 471/04

\* cited by examiner

*Primary Examiner* — Charanjit Aulakh
(74) *Attorney, Agent, or Firm* — PatentScience LLC; Jay R Akhave

(57) ABSTRACT

The present invention relates to a process for the preparation of Trametinib acetic acid solvate (Ia): The present invention also directed towards a pharmaceutical composition comprising Trametinib acetic acid solvate (Ia) and optionally one or more pharmaceutically acceptable excipients or carriers.

Formula Ia

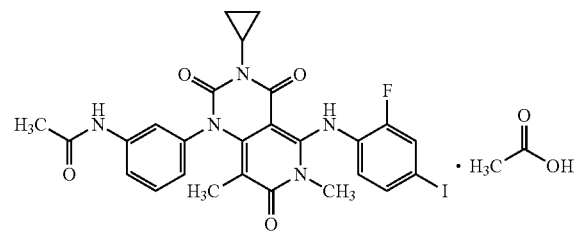

7 Claims, 3 Drawing Sheets

PROCESS FOR THE PREPARATION OF TRAMETINIB ACETIC ACID SOLVATE

FIELD OF INVENTION

The present invention relates to crystalline Form of an acetic acid solvate of Trametinib of Formula (I).

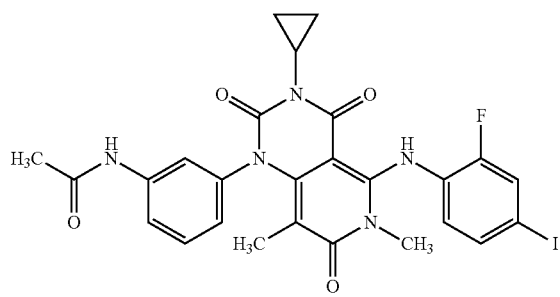

Formula I

The structure of the Trametinib acetic acid solvate (Ia) is shown below:

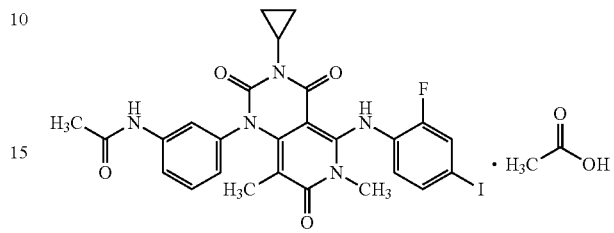

Formula Ia

BACKGROUND OF THE INVENTION

Trametinib (I) is chemically known as N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-1]-phenyl}acetamide. Dimethyl sulfoxide solvate of Trametinib (I) is a kinase inhibitor and is indicated for the treatment of patients with unresectable or metastatic melanoma with BRAF V600E or V600K mutations. Trametinib products are currently being marketed under the brand name Mekinist®.

Trametinib is first disclosed in U.S. Pat. No. 7,378,423. According to US '423 Trametinib is prepared staring from 2-fluoro-4-iodoaniline (II) as shown below:

Scheme-I

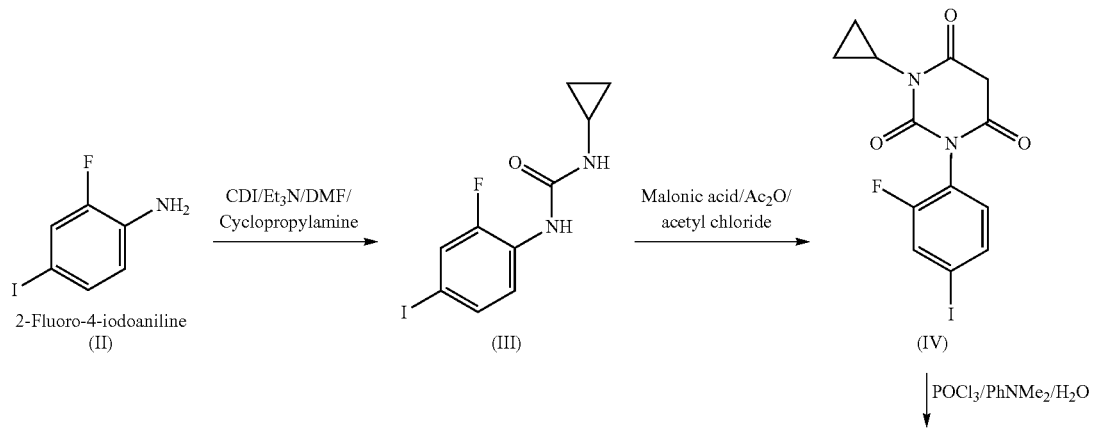

-continued
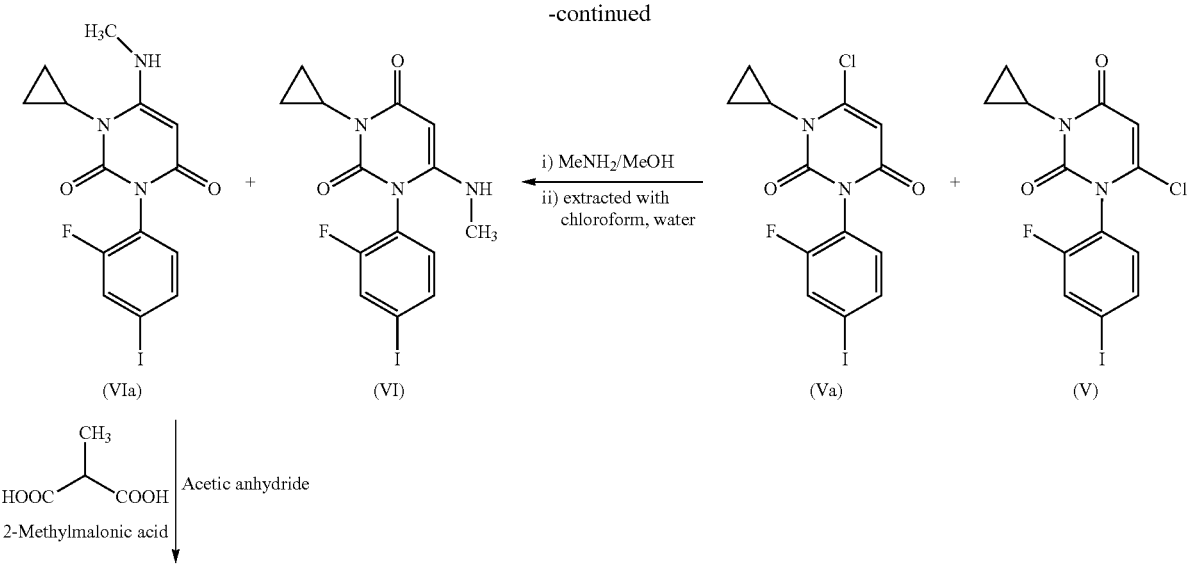
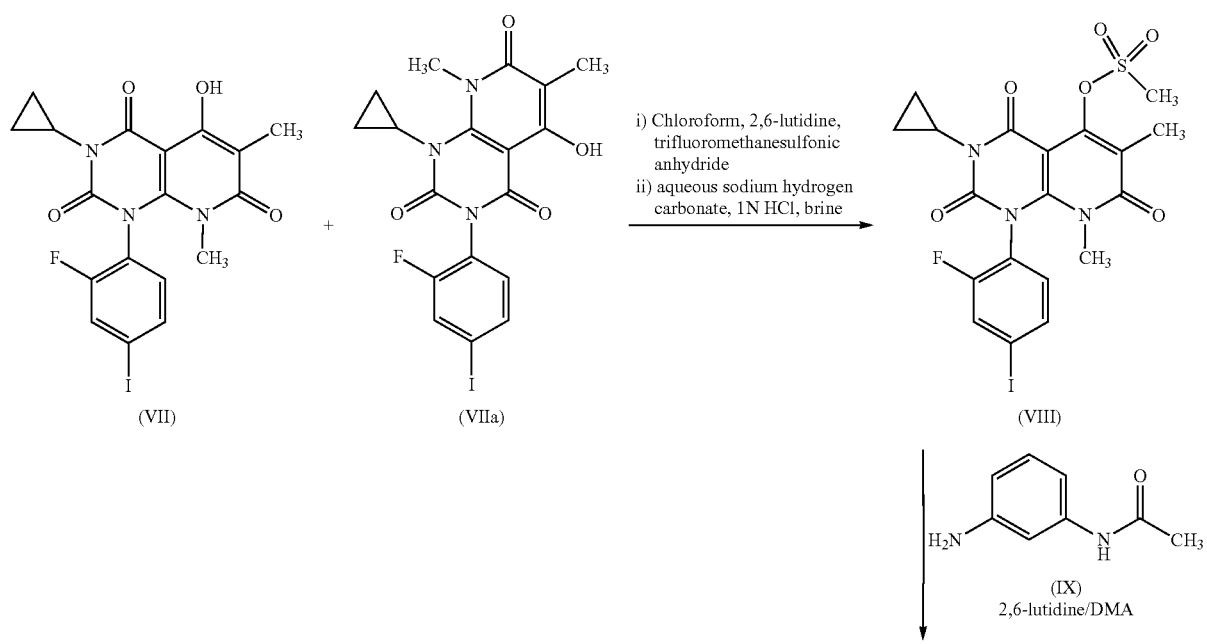
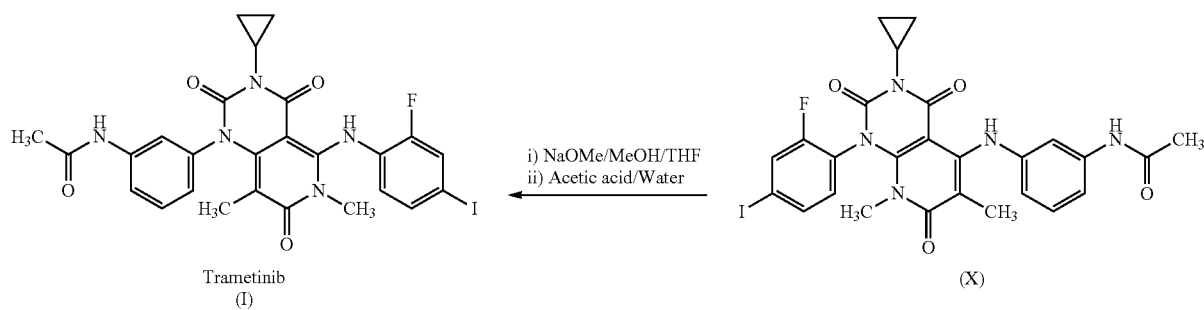

US '423 also discloses an alternate process for the preparation of the intermediate compound (X), which is converted to Trametinib (I) in the same manner as shown in Scheme (I). The process is as shown below:
Scheme-II
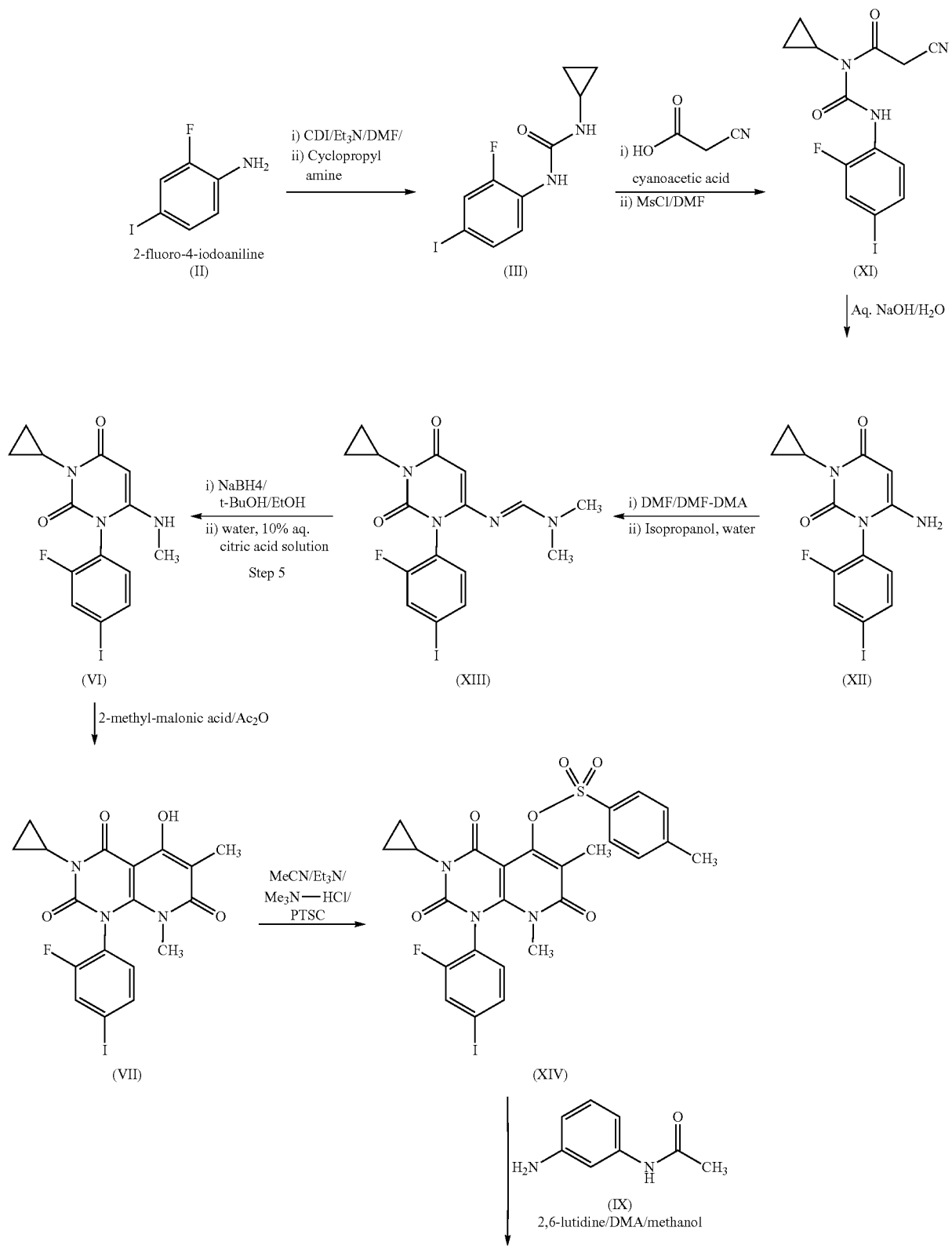

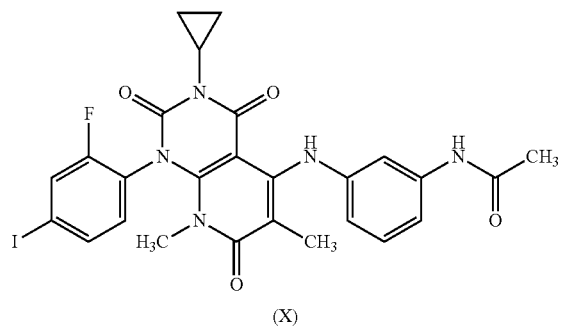

(X)

US '423 also discloses the Trametinib solvate forms such as acetic acid solvate, dimethylsulfoxide solvate, ethanol solvate, nitromethane solvate, chlorobenzene solvate, 1-pentanol solvate, isopropyl alcohol solvate, ethylene glycol solvate and 3-methylbutanol solvate. However, this patent does not disclose any specific process for preparing the above mentioned Trametinib solvates.

WO 2015/081566 A1 discloses the Trametinib solvate forms such as ethanol, n-propanol, tetrahydrofuran (THF), trifluoroethanol, acetone, tert-butyl ether and DMSO. All these solvates are prepared by sonicating method from amorphous form of Trametinib.

IN 5116/CHE/2014 discloses Trametinib benzyl alcohol solvate and Trametinib ethyl acetate solvate. These solvates are prepared by heating and cooling of Trametinib reaction mixture.

U.S. Pat. No. 8,580,304 discloses solid oral pharmaceutical dosage forms, suitably tablets, suitably capsules, comprising Trametinib dimethyl sulfoxide solvate. The composition comprises Trametinib dimethyl sulfoxide solvate, about 25% to about 89% by weight of one or more excipients, where the excipients are substantially free of water; and the amount of unsolvated drug does not exceed about 20%.

US20170014414 A1 discloses pharmaceutical composition comprising Trametinib or a pharmaceutically acceptable salt thereof as active ingredient and a carrier, characterized in that the carrier forms a matrix in which the active ingredient is embedded.

US20170020880 A1 discloses pharmaceutical composition comprising Trametinib or its pharmaceutically acceptable salt or solvate and greater than or equal to 90% of pharmaceutically acceptable excipients, based on the total weight of the composition, wherein the excipients comprise a solubility enhancer.

US20150328320 A1 discloses direct powder blend formulation comprising Trametinib dimethyl sulfoxide solvate and a solubilizer.

However, there is a need to develop a cost effective and commercially viable process to produce Trametinib acetic acid solvate (Ia) having a known impurity≤0.05% (desiodo) and other unknown impurities≤0.06%.

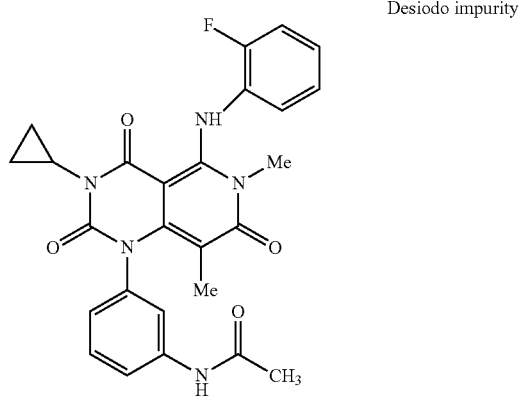 [SMILES: CC(=O)Nc1cccc(-n2c(=O)n(C3CC3)c(=O)c3c(Nc4ccccc4F)n(C)c(=O)c(C)c32)c1]

Desiodo impurity

The advantage of the present invention is it can eliminate carry over impurities while preparing solvate, operationally viable in commercial scale and higher yield and purity.

The present invention is directed towards crystalline Trametinib acetic acid solvate (Ia) and a process for the preparation of crystalline Form of Trametinib acetic acid solvate (Ia) involves, reacting Trametinib with acetic acid at suitable temperature and isolating pure crystalline Trametinib acetic acid solvate (Ia).

The present invention also directed towards a pharmaceutical composition comprising Trametinib acetic acid solvate (Ia) and optionally one or more pharmaceutically acceptable excipients or carriers.

OBJECTIVE OF INVENTION

The main objective of the present invention is to provide a simple and cost effective process for the preparation of crystalline Form of Trametinib acetic acid solvate (Ia) which is industrially viable.

SUMMARY OF THE INVENTION

The main embodiment of the present invention is to provide a crystalline Form of Trametinib acetic acid solvate (Ia), characterized by

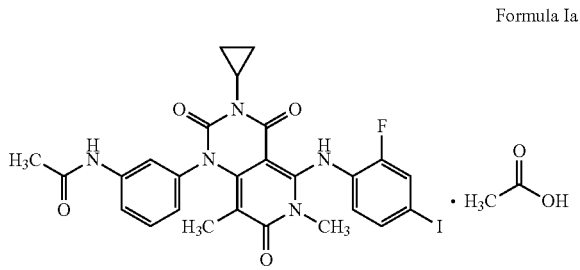

Formula Ia

X-ray diffraction pattern substantially as shown in FIG. 1;
DSC as shown in FIG. 2; and
TGA as shown in FIG. 3.

The crystalline Trametinib acetic acid solvate (Ia) has a purity of ≥99.5%.

The crystalline Trametinib acetic acid solvate (Ia) characterized by:
  X-ray diffraction pattern having characteristic peaks at 5.2, 9.1, 10.4, 10.7, 12.1, 12.8, 13.7, 15.9, 18.1, 18.6, 19.3, 19.9, 20.9, 21.2, 22.1, 22.9, 24.6, 25.9, 27.8±0.2 angle 2θ;
  DSC having onset temperature at 179° C. and 187° C.; having peak at 189° C. and 197° C. and end set temperature at 198° C. and 201° C.;
  TGA as shown in FIG. 3.

Another embodiment of the present invention is to provide a process for the preparation of crystalline Trametinib acetic acid solvate (Ia) having purity of ≥99.5%,

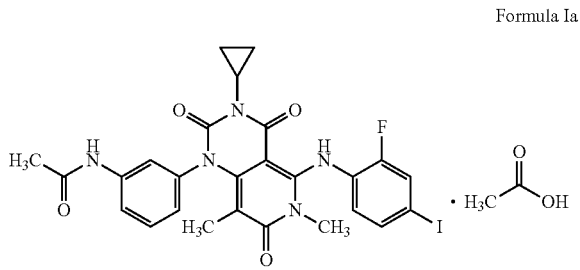

Formula Ia which comprises:
  (i) treating Trametinib with acetic acid at suitable temperature;
  (ii) heating the reaction mixture to get a clear solution; and
  (iii) isolating pure crystalline Trametinib acetic acid solvate (Ia).

Yet another embodiment of the present invention is to provide a pharmaceutical composition comprising Trametinib acetic acid solvate (Ia) having purity of ≥99.5% and optionally one or more pharmaceutically acceptable excipients or carriers.

DETAILED DESCRIPTION OF THE INVENTION

The main embodiment of the present invention is to provide a crystalline Form of Trametinib acetic acid solvate (Ia), characterized by

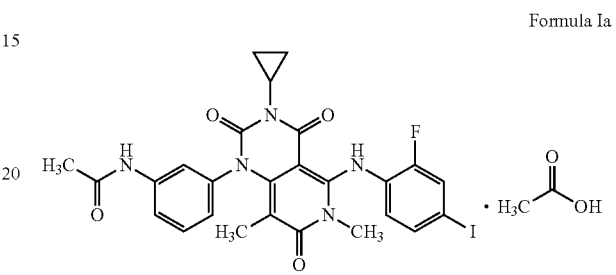

Formula Ia

Figure 1:
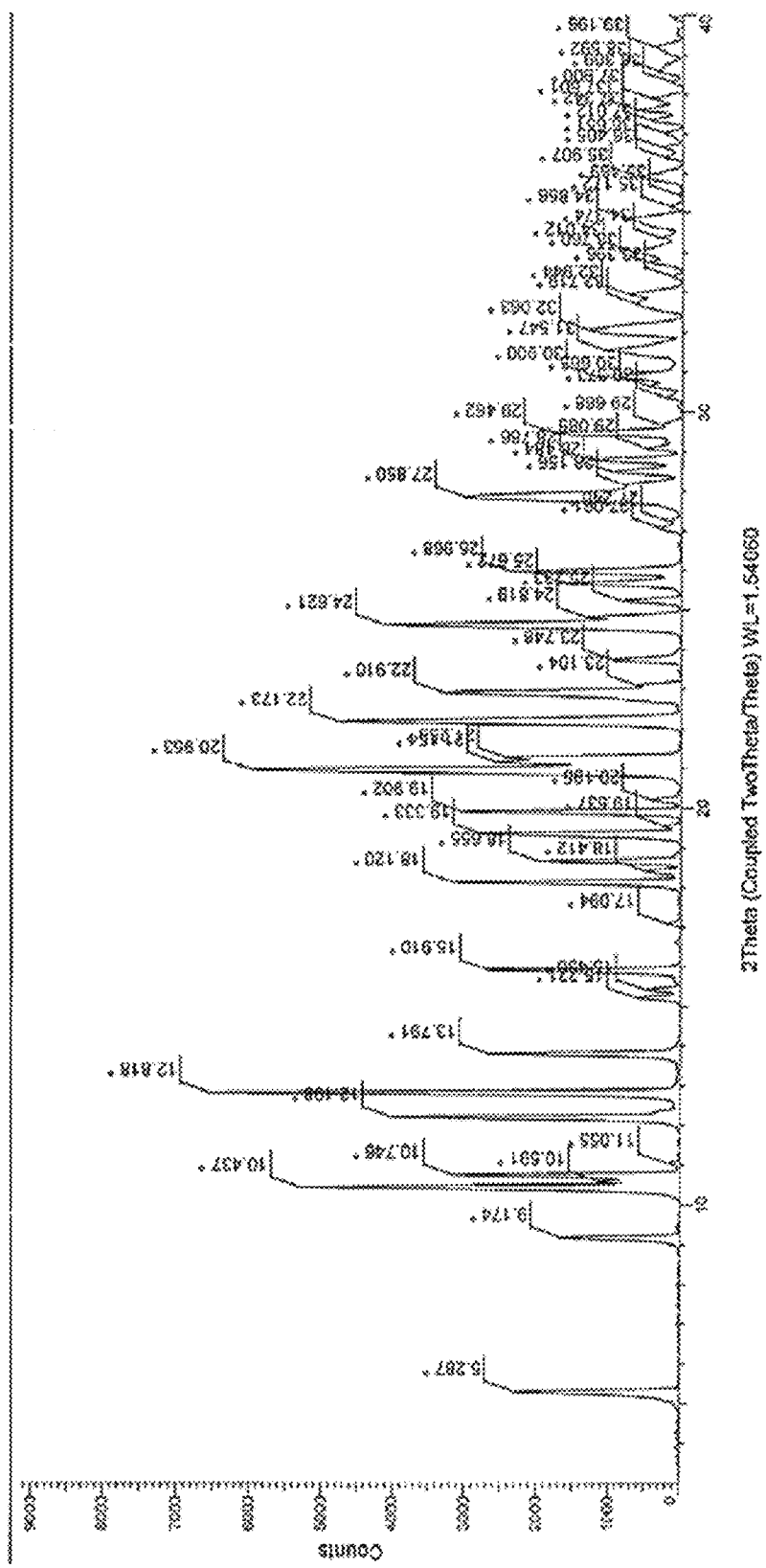
FIG. 1 Illustrates the X-ray powder diffraction pattern of crystalline form of Trametinib acetic acid solvate (Ia) produced by the present invention.
Figure 2:
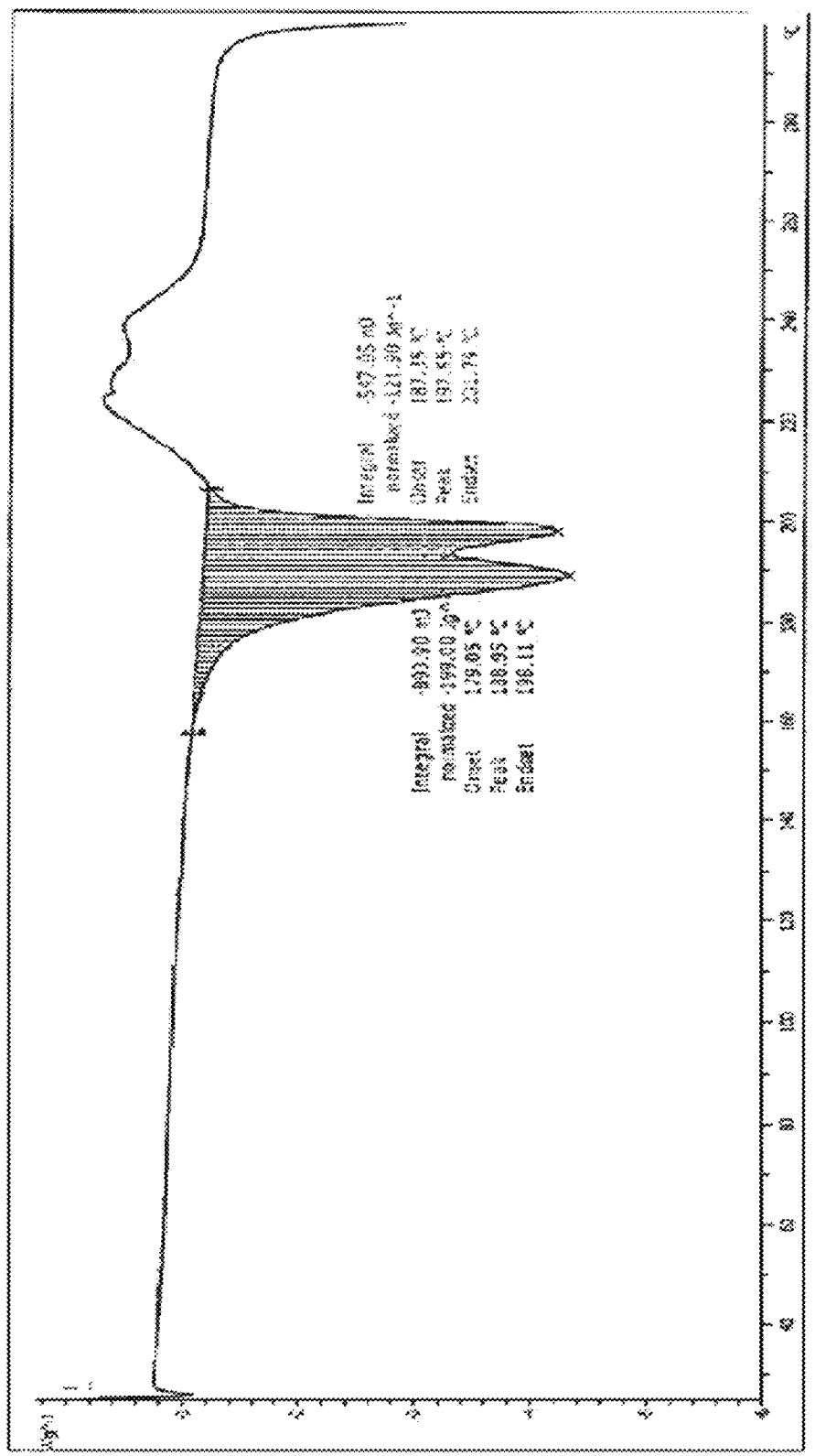
FIG. 2 Illustrates the DSC of Trametinib acetic acid solvate (Ia) produced by the present invention.
Figure 3:
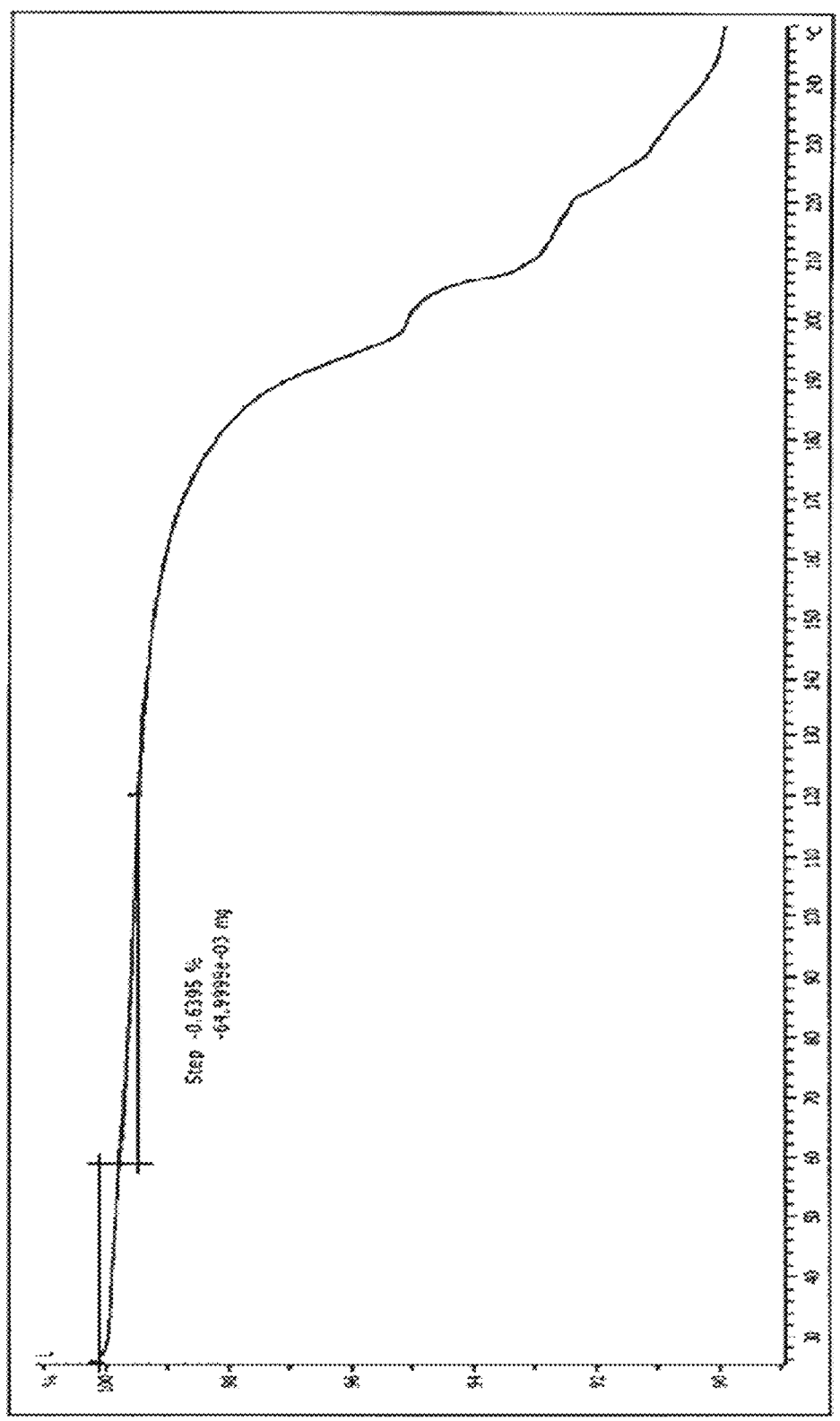
FIG. 3 Illustrates the TGA of Trametinib acetic acid solvate (Ia) produced by the present invention.

X-ray diffraction pattern substantially as shown in FIG. 1;
DSC as shown in FIG. 2; and
TGA as shown in FIG. 3.

The crystalline Trametinib acetic acid solvate (Ia) has a purity of ≥99.5%.

The crystalline Trametinib acetic acid solvate (Ia) characterized by:
  X-ray diffraction pattern having characteristic peaks at 5.2, 9.1, 10.4, 10.7, 12.1, 12.8, 13.7, 15.9, 18.1, 18.6, 19.3, 19.9, 20.9, 21.2, 22.1, 22.9, 24.6, 25.9, 27.8±0.2 angle 2θ;
  DSC having onset temperature at 179° C. and 187° C.; having peak at 189° C. and 197° C. and end set temperature at 198° C. and 201° C.;
  TGA as shown in FIG. 3.

The crystalline Trametinib acetic acid solvate (Ia), further characterized by X-ray diffraction pattern having angle 2θ values at 10.5, 11.0, 15.2, 15.4, 17.0, 18.4, 19.5, 20.1, 21.1, 23.1, 23.7, 24.8, 25.2, 25.6, 27.0, 27.2, 28.1, 28.4, 28.7, 29.0, 29.6, 30.3, 30.6, 30.9, 31.5, 32.0, 32.7, 32.9, 33.3, 33.7, 34.0, 34.3, 34.8, 35.1, 35.4, 35.9, 36.4, 36.6, 37.0, 37.3, 37.6, 37.9, 38.3, 38.5, 39.1 and 39.9±0.2.

Another embodiment of the present invention is to provide a process for the preparation of Trametinib acetic acid solvate (Ia) having purity of ≥99.5%.

The process comprises, treating Trametinib (I) with acetic acid at suitable temperature, heating the reaction mixture to get a clear solution and isolating Trametinib acetic acid solvate (Ia) upon cooling.

The acetic acid is added to Trametinib (I) at room temperature. Then heating to get clear solution takes place at a temperature ranges from 95° C. to 115° C. After filtration, the filtrate is cooled to room temperature. The precipitate is filtered and dried to get Trametinib acetic acid solvate (Ia).

The Trametinib acetic acid solvate (Ia) is isolated as crystalline form having purity of ≥99.5%.

Yet another embodiment of the present invention is to provide a pharmaceutical composition comprising crystalline Trametinib acetic acid solvate (Ia) having purity of ≥99.5% and optionally one or more pharmaceutically acceptable excipients or carriers.

The pharmaceutically acceptable excipient or carrier comprises a diluent and/or a binder and/or a lubricant and/or a disintegrant.

Diluents include, but are not limited to water-soluble fillers and water-insoluble fillers, such as calcium phosphate (e.g., di and tri basic, hydrated or anhydrous), calcium sulfate, calcium carbonate, magnesium carbonate, kaolin, lactose, cellulose (e.g., microcrystalline cellulose, powdered cellulose), pregelatinized starch, starch, lactitol, mannitol, sorbitol, maltodextrin, powdered sugar, compressible sugar, sucrose, dextrose, and inositol. The pharmaceutical composition of the present invention comprises one or more diluent from about 30% to about 90% by weight of the composition.

Binders include, but are not limited to hydroxypropyl methyl cellulose (HPMC), hydroxypropyl cellulose (HPC), hydroxyethyl cellulose (HEC) and ethyl cellulose (EC)], polyvinylpyrrolidone. Binders that are substantially free of water are suitable for tablets of the current invention. In one embodiment of the present invention, the binder is hydroxypropyl methyl cellulose (HPMC) or Hypromellose. The pharmaceutical composition of the present invention comprises binder from about 2% to about 10% by weight of the composition.

Lubricants include, but are not limited to talc, stearates (e.g., magnesium stearate, calcium stearate, zinc stearate, palmitostearate), stearic acid, hydrogenated vegetable oils, glyceryl behenate, polyethylene glycol, ethylene oxide polymers (e.g., CARBOWAXes), liquid paraffin, sodium lauryl sulfate, magnesium lauryl sulfate, sodium oleate, sodium stearyl fumarate, DL-leucine, and silica derivatives (e.g., colloidal silicon dioxide, colloidal silica, pyrogenic silica, and sodium silicoaluminate). The pharmaceutical composition of the present invention comprises lubricant from about 0.5% to about 2% by weight of the composition.

Disintegrants include, but are not limited to starches, celluloses, gums, crosslinked polymers, and effervescent agents, such as corn starch, potato starch, pregelatinized starch, modified corn starch, croscarmellose sodium, crospovidone, sodium starch glycolate, Veegum HV, methyl cellulose, microcrystalline cellulose, cellulose, colloidal silicon dioxide, modified cellulose gum (e.g., Ac-Di-Sol R), agar, bentonite, montmorillonite clay, natural sponge, cation exchange resins, ion exchange resins (e.g., polyacrin potassium), alginic acid and alginates, guar gum, citrus pulp, carboxymethylcellulose and salts, sodium lauryl sulfate, magnesium aluminum silicate, hydrous aluminum silicate, sodium bicarbonate in admixture with an acidulent such as tartaric acid or citric acid. The pharmaceutical composition of the present invention comprises one or more disintegrant from about 1% to about 5% by weight of the composition.

The pharmaceutical composition of the present invention can be solid dosage form (e.g. powder or tablet or capsule etc.) or semisolid dosage form (e.g. cream or ointment etc.) or liquid (e.g. solution or suspension or emulsion or injection etc.) is prepared by methods known in the art including but not limited to wet granulation or dry granulation or direct compression.

Trametinib (I) used in this invention is prepared according to the process disclosed in U.S. Pat. No. 7,378,423.

The following example(s) illustrate the nature of the invention and are provided for illustrative purposes only and should not be construed to limit the scope of the invention.

EXAMPLE-1

Preparation of Trametinib Acetic Acid Solvate

N-{3-[3-Cyclo-propyl-5-(2-fluoro-4-iodo-phenyl)-6,8-dimethyl-2,4,7-trioxo-3,4,6,7-tetrahydro-2H-pyrido[4,3-D]pyrimidin-1-yl]-phenyl}-acetamide (5 g, Trametinib) was suspended in acetic acid (50 ml) at 25-30° C. The suspension was heated to 105-110° C. to get a clear solution. The solution obtained was cooled to 100° C. and carbon (0.5 g) was added followed by stirred for 15 min. The acetic acid solution was filtered through hyflo bed, the bed was washed with hot acetic acid (10 ml, 50° C.). The filtrate was cooled to 25-30° C. and stirred for 2 hrs at 25-30° C. The precipitate obtained was filtered, washed with acetic acid (5 ml) at 25-30° C. and dried under reduced pressure at 45-50° C. (Output: 4.7 g).

Yield: 85%

Chromatographic purity: >99.8%

We claim:
1. Crystalline Form of Trametinib acetic acid solvate (Ia), characterized by

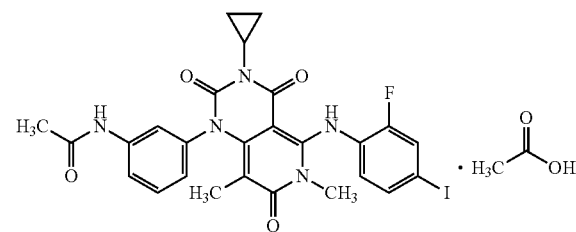

Formula Ia with X-ray diffraction pattern, having characteristic peaks at 5.2, 10.4, 12.8, 20.9, 22.1, 24.6 and 27.8±0.2 angle 2θ.

2. The crystalline Trametinib acetic acid solvate (Ia) as claimed in claim 1, which is characterized by X-ray diffraction pattern having further characteristic peaks at 9.1, 10.7, 12.1, 13.7, 15.9, 18.1, 18.6, 19.3, 19.9, 21.2, 22.9, 25.9, angle 2θ.

3. The crystalline Trametinib acetic acid solvate (Ia) as claimed in claim 1, which is characterized by a DSC having onset temperature at 179° C. and 187° C.; having peak at 189° C. and 197° C. and end set temperature at 198° C. and 201° C.

4. The crystalline Trametinib acetic acid solvate (Ia) as claimed in claim 1, has a purity of ≥99.5%.

5. A process for the preparation of crystalline Form of Trametinib acetic acid solvate (Ia), of claim 4 having purity of ≥99.5%;

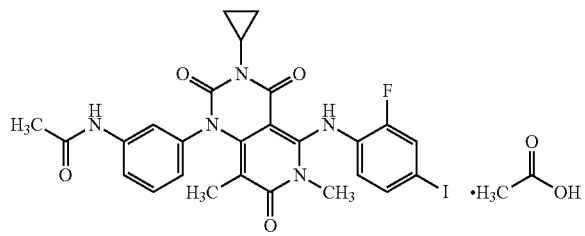

Formula Ia which comprises:
(i) treating Trametinib with acetic acid at suitable temperature;
(ii) heating the reaction mixture to get a clear solution; and (iii) isolating pure crystalline Trametinib acetic acid solvate (Ia).

6. The process as claimed in claim 5, wherein step (i) is carried at suitable temperature ranges from 95° C. to 115° C.

7. An oral pharmaceutical composition comprising crystalline Form of Trametinib acetic acid solvate (Ia) as claimed in claim 1 and a pharmaceutically acceptable excipient or carrier.

\* \* \* \* \*